US005811296A

United States Patent [19]

Chemelli et al.

[11] Patent Number: 5,811,296

[45] Date of Patent: Sep. 22, 1998

[54] BLOCKED COMPARTMENTS IN A PCR REACTION VESSEL

[75] Inventors: John Benjamin Chemelli, Webster; Charles Cullis Hinckley, Fairport, both of N.Y.

[73] Assignee: Johnson & Johnson Clinical Diagnostics, Inc., Rochester, N.Y.

[21] Appl. No.: 770,831

[22] Filed: Dec. 20, 1996

[51] Int. Cl.[6] .............................. C12P 19/34; G01N 1/10; B65D 1/24; B65B 51/10

[52] U.S. Cl. .......................... 435/287.2; 435/6; 435/91.2; 435/288.2; 435/288.5; 422/58; 422/102; 206/223; 206/569

[58] Field of Search ........................... 435/91.2, 6, 287.2, 435/288.2, 288.5; 356/246; 220/521; 53/477; 422/58, 102; 206/223, 569

[56] References Cited

U.S. PATENT DOCUMENTS 5,422,271 6/1995 Chen et al. ............................ 435/287

FOREIGN PATENT DOCUMENTS 0 693 560 A2 1/1996 European Pat. Off. .......... C12Q 1/68

*Primary Examiner*—Kenneth R. Horlick
*Assistant Examiner*—Joyce Tung
*Attorney, Agent, or Firm*—Dana M. Schmidt

[57] ABSTRACT

A flexible cuvette comprising enclosed chambers and passageways for filling and/or passing liquid thereinto or therethrough, the chambers and passageways being formed by plastic sheets blocked together prior to use to eliminate air bubbles, by an amount sufficient to require at least 0.8 g/cm of lineal width peel-apart force.

7 Claims, 5 Drawing Sheets

BLOCKED COMPARTMENTS IN A PCR REACTION VESSEL

FIELD OF THE INVENTION

This invention relates to a cuvette and method of making such wherein compartments empty prior to use are formed to be free of air.

BACKGROUND OF THE INVENTION

A number of patents have been granted describing a flexible cuvette or pouch for doing nucleic acid material amplification and detection in a closed, contained environment. A recent example is U.S. Pat. No. 5,422,271. In such cuvettes, two flexible sheets are formed and sealed together to define sealed compartments connected by passageways to conduct liquids providing the desired reactions. Those compartments include a reaction chamber, waste collection chamber, and a detection chamber having therein at least one immobilized detection reagent. Those named chambers preferably start out otherwise nominally empty, although the reaction chamber can have reagents pre-incorporated therein.

One problem that has occurred during manufacturing is that those compartments, under conventional manufacturing techniques, tend to end up with air in them prior to use. That is, they are blisters of air, and the air creates air bubbles when liquid flows into them. Air bubbles in the passageways are a problem in preventing necessary passage of liquid as desired. Air bubbles in the detection chamber can interfere by preventing liquid reagents and sample from uniformly reaching the immobilized detection reagents.

Therefore, there has been a problem, prior to this invention, in supplying ready-to-use flexible cuvettes as described above, wherein "empty" compartments are truly empty rather than containing air. The need has been to correct this problem.

SUMMARY OF THE INVENTION

We have discovered a cuvette construction, and a method of assembly, which ensure that the amount of air left in the manufactured cuvette's "empty" compartments prior to use, is minimized.

More specifically, in accord with one aspect of the invention, there is provided a flexible reaction cuvette comprising opposed plastic sheets sealed together to define expandable compartments comprising a sample reaction chamber, a detection chamber, a waste collection chamber, a first passageway between the reaction chamber and the detection chamber, and a second passageway between the detection chamber and said collection chamber. The cuvette is improved in that the sheets are blocked together in the regions of at least the reaction chamber, the collection chamber, and the passageways by an amount sufficient to require at least 0.8 g/cm of width lineal peel-apart force when peeled at a 90 degree angle, to separate the sheets at the chambers or passageways;

so that air bubbles are eliminated from the chambers and the passageways prior to initiating flow of liquid into them.

In accord with another aspect of the invention, there is provided a method of forming a sealed compartment between two flexible, plastic sheets so as to eliminate air within the compartment without permanently adhering the sheets together to prevent liquid from entering the compartment.

The method comprises the steps of:

a) selecting two sheets of plastic having together a heat seal temperature effective to produce the permanent adherence, b) pressing the sheets together uniformly with a pressure of at least about 300 kPa;

c) heating the sheets in a region of a compartment to a temperature that is sufficient to block the sheets together at the compartment with an attraction requiring a peel-apart force of between about 0.8 and about 6 g/cm of lineal width when peeled at a 90° angle, and is less than the heat seal temperature; and d) heat-sealing the sheets together at at least the heat seal temperature, around at least a portion of the perimeter of the compartment to create a permanent adherence at the perimeter portion.

Accordingly, it is an advantageous feature of the invention that flexible cuvettes can be formed so that nominally empty compartments and passageways truly are empty prior to use—that is, they contain no entrapped air.

It is a related advantageous feature of the invention that such compartments and passageways are substantially free of air bubbles during use with liquids, and have a collapse memory that tends to force liquids out of them in the absence of incoming pressure.

Another advantageous feature of the invention is that such compartments, by virtue of their blocking, tend to resist surging when liquid is first forced into them under pressure.

Other advantageous features will become apparent upon reference to the following Detailed Description, when read in light of the attached drawings.

DESCRIPTION OF THE PREFERRED EMBODIMENTS

The invention is described herein in connection with preferred embodiments, wherein a cuvette of a preferred configuration, using preferred plastics, is assembled for a closed reaction process such as PCR amplification and detection. In addition, the invention is useful regardless of the configuration of the cuvette and the shape, number or sizes of compartments, regardless of which flexible plastics are used to assemble the cuvette, and regardless of the end use of the cuvette, so long as certain compartments therein are blocked together during assembly. As used herein, "blocking" or "blocked" means, an attraction that requires a peel-apart force when peeled at a 90° angle, that is between about 0.8 g/cm of lineal width and about 6 g/cm of lineal width. (This distinguishes over normal "static cling" that can exist when two plastic sheets are simply placed in contact, since the peel-apart force in such a case is less than 0.8 g/cm of lineal width.)

Figure 1:
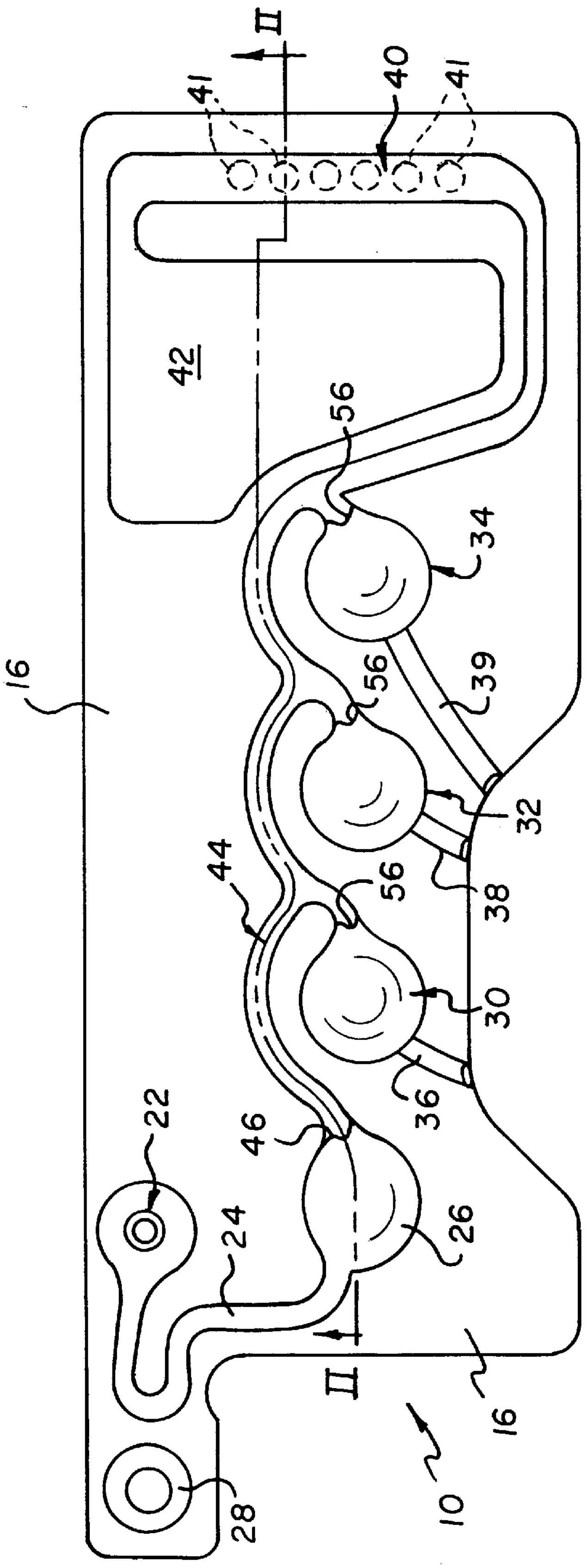
FIG. 1 is a plan view of a cuvette with which the invention is useful.

Thus, a preferred flexible cuvette 10, FIG. 1, prepared in accordance with the invention comprises, as described for example in the aforesaid '271 patent, an inlet port 22 for injection of patient sample liquid, which connects via a passageway 24 to a PCR reaction compartment 26. A seal 46 temporarily blocks flow out of compartment 26. When seal 46 is broken, liquid feeds via a passageway 44 to a detection chamber 40 having sites 41 comprising, preferably, beads anchored in place which will attach to any targeted analyte passing them from compartment 26, and then the analyte attaches to reagents coming from the other reagent compartments. Those other compartments are compartments 30,32,34, each feeding via passageways 48 and 50 to chamber 40. Each of those passageways is temporarily sealed at 56, and contains an appropriate reagent liquid.

The details of the chemicals useful in all the compartments, and at the sites 41, are explained in more detail in said '271 patent.

Figure 2:
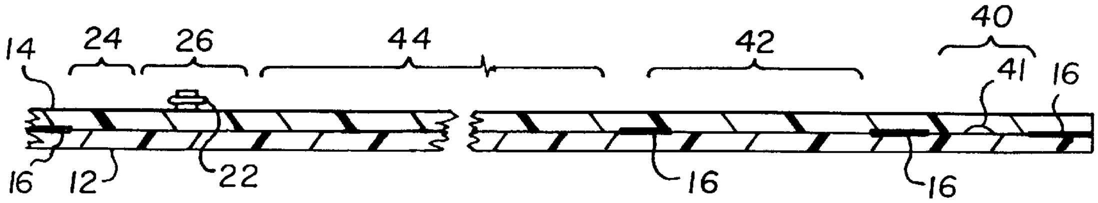
FIG. 2 is a fragmentary section view taken along the lines II—II of FIG. 1, prior to introduction of any liquid into the cuvette by the user.

The two sheets 12,14 of plastic comprising the cuvette are heat-sealed at areas 16 for permanent adhesion, FIG. 2, at all areas except the port 22, FIG. 1, reaction compartment 26, reagent compartments 30–34, passageways 24,44, detection compartment 40, and waste collection chamber 42. These instead are prepared so that all but compartments 30,32,34, and inlet port 22, are blocked together as herein defined. Inlet port 22, of course, has to be open to allow liquid injection (followed by permanent closure using closure portion 28 that is folded over to engage and close port 22). Compartments 30,32,34 are pre-filled with reagent liquids, using paths 36,38,39, respectively, that are sealed after filling. Hence, these compartments are shown, FIG. 1, as domed. However, the portions 24,26,40,42,44 are substantially flat, i.e., substantially free of air, FIG. 2, as manufactured, because they are blocked together.

In addition to the peel-apart force required to peel apart those portions blocked together as described herein, the "blocking" can be further identified from the finished product by the sheen produced.

Figure 3:
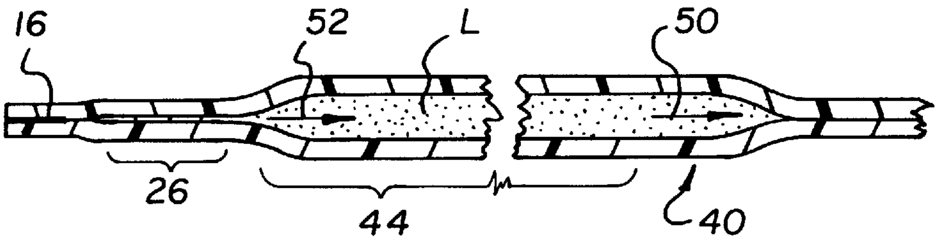
FIG. 3 is a section view similar to that of FIG. 2, after liquid has been expelled from the reaction compartment.

During use, such as is described in the aforesaid '271 patent, FIG. 3, the portions that are blocked are forced open by a surge, arrow 50, of liquid L forced out of various compartments in sequence, that proceeds to sites 41 and then on to compartment 42 (not shown). As the last of the liquid, arrow 52, leaves the now unblocked portion, e.g., compartment 26, that portion's plastic memory of its blocked condition tends to force that portion closed.

Figure 4:
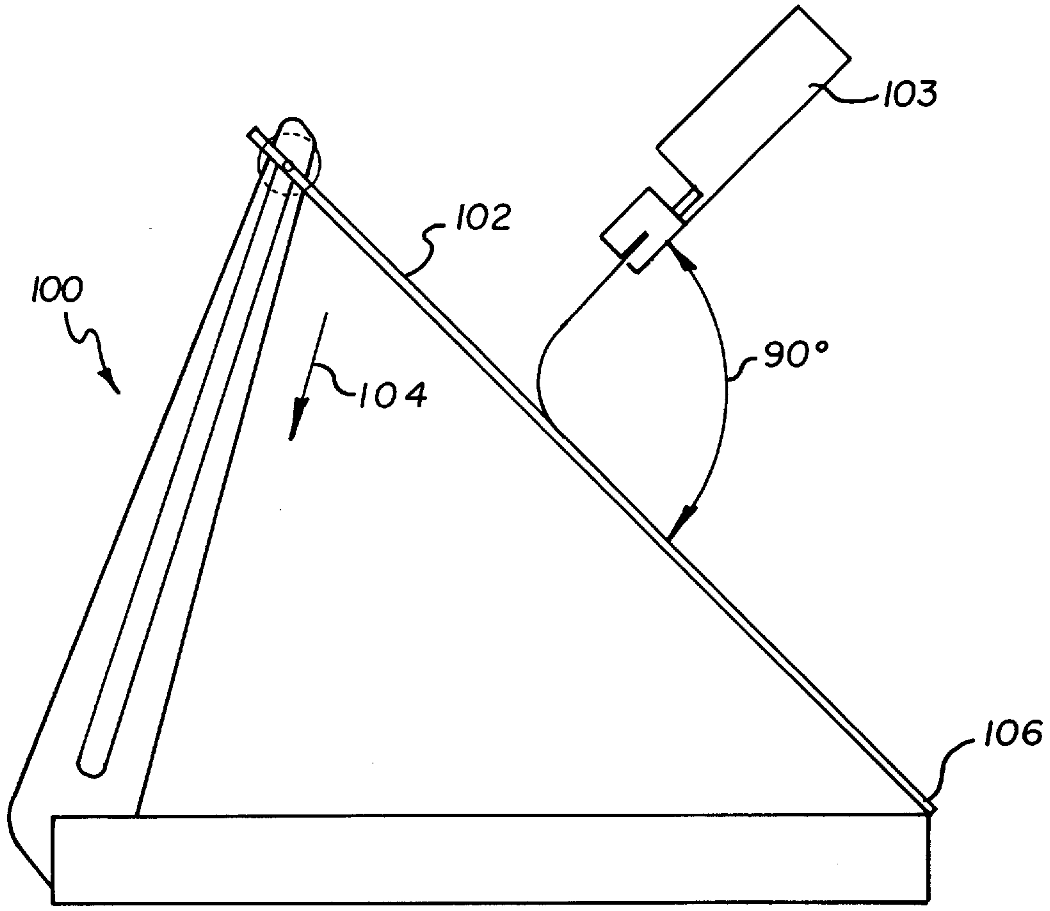
FIG. 4 is an elevational view of the test device for determining the peel-apart force used to define blocking herein.

The peel-apart force is measured by test apparatus such as that shown in FIG. 4. That is, a platform 100 is created with a support surface 102, and the two sheets of plastic to be tested are mounted thereon so that the bottom sheet is adhered to surface 102. The topmost of the two sheets is gripped along its entire width, which is preferably 2.54 cm, in a transducer 103 held rigidly in place, and the support 102 is pivoted away, arrow 104, at a preferred rate of about 30.5 cm per minute, about pivot 106, from transducer 103 while maintaining a 90° angle. The force required to peel apart the two sheets is measured and expressed in g/per lineal width of sheet.

Figure 5:
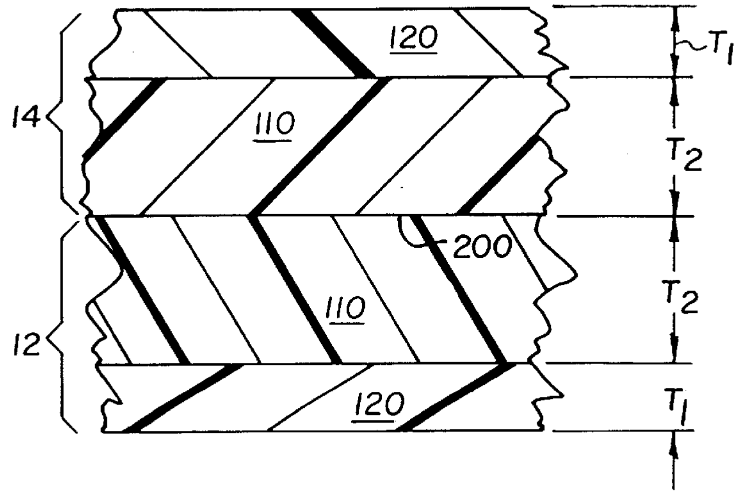
FIG. 5 is an enlarged fragmentary section view similar to that of FIG. 2, showing a laminate construction.

The preferred blocking of the invention as defined by the above-noted peel-apart force, is achieved by uniformly pressing the two opposed sheets of plastic together while heating to a temperature less than the heat-sealing temperature producing permanent adhesion. Such temperatures and pressures are, of course, a function of the plastics chosen, and are readily determinable by those skilled in the art. Since a variety of plastics and then thickness are useful, so a variety of blocking temperatures, and pressures, can be used. FIG. 5 illustrates a useful example. That is, each of sheets 14 and 12 is preferably a laminate of polyethylene 110, hereinafter "PE", and oriented polyethylene terephthalate 120, hereinafter "PET", of thicknesses $T_2$ and $T_1$, respectively, oriented so that the PE portions are blocked together at portion 200. (As used herein, PE has a specific gravity within the range of about 0.918 to about 0.94 based on ASTM D792.)

The pressing is done with pressure jaws of an appropriate shape. The jaws have enough compliance, or are uniformly flat as a metal surface, sufficient to ensure intimate uniform contact with the plastic sheets at the desired blocking areas. Because uniform flatness of the metal jaws themselves is difficult to achieve, the preferred design is jaws having on their opposing surfaces, a thin elastomeric coating having a durometer value of about 30 durometer Shore "A". Such compliant coating provides the intimate contact needed. In a highly-preferred example, the coating is a silicone rubber that is from 0.254 cm to 0.5 cm thick, obtained under the trade name "RTV-700" from General Electric.

Figure 6:
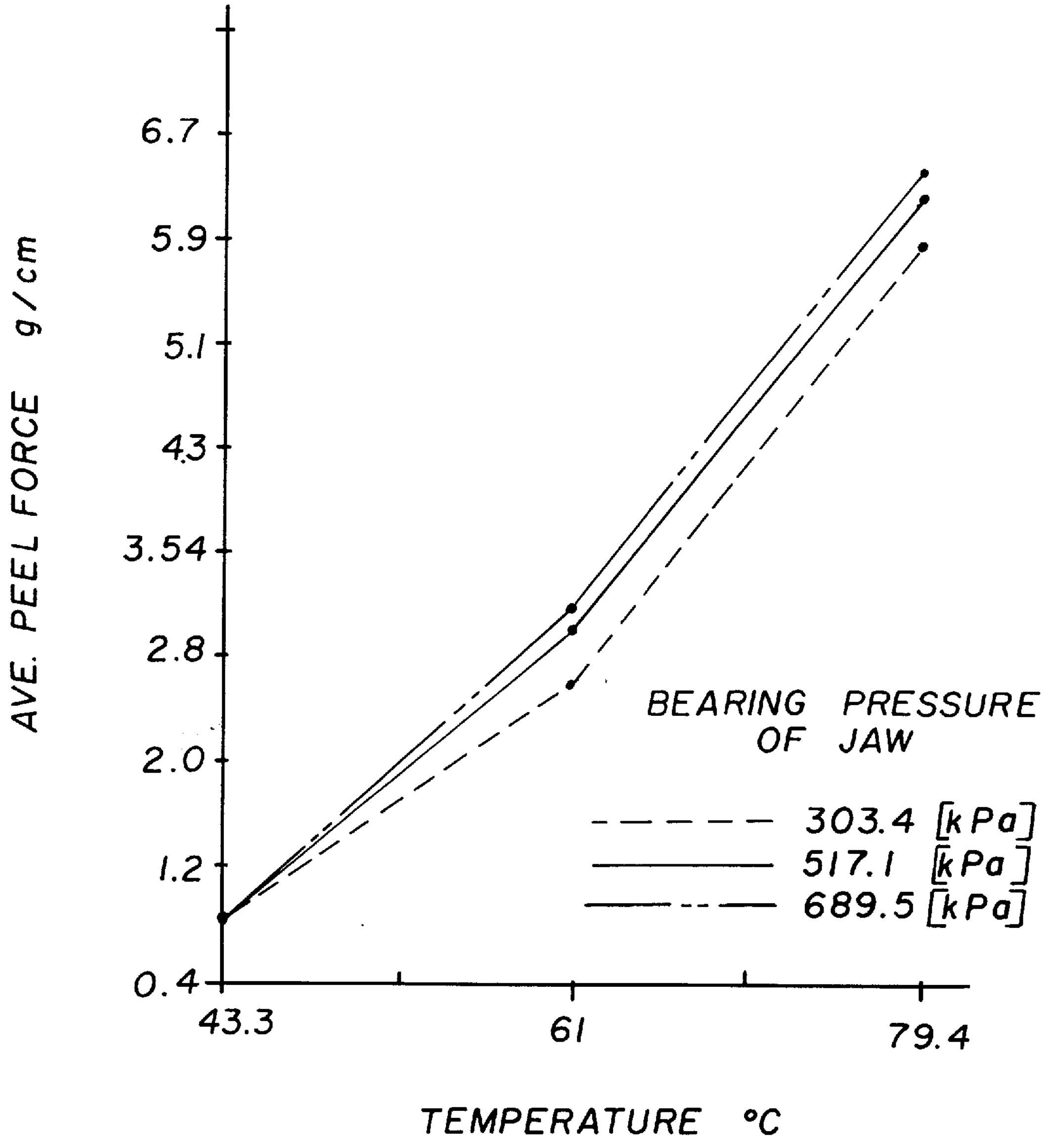
FIGS. 6 and 7 are plots of the temperatures used to achieve the desired blocking of the invention, in two different embodiments.

In the example that follows, $T_2$ is about 0.09 mm and $T_1$ is about 0.013 mm, but other thicknesses are obviously useful. For this example, in the case where sheets 12,14 are chosen, as a preferred example, from a laminate of polyethylene having a specific gravity between about 0.926 and 0.94, and oriented polyethylene terephthalate having a thickness between about 0.013 mm and 0.04 mm, the pressures and temperature selected were those shown in FIG. 6. Thus, the pressure pushing the sheets together is not very significant as the results tend to vary a little, even when going from about 300 to about 690 kilopascals (kPa) of pressure. However, the temperature should be between about 43° and 85° C., as above 85° C., permanent adhesion starts to occur. The time for the blocking reaction to occur in this example is about 3 sec.

The order of assembly of the vessel is thus preferably as follows:

First, the detection sites 41 are deposited on one of the two sheets. Then, both sheets 12 and 14 are blocked together over the entire vessel (except for the port 22), using the pressure jaws and blocking temperatures described above. Thereafter, the vessel is moved to a different set of pressure jaws, configured to form the permanent seal areas 16, which different set of jaws is heated to the permanent sealing temperatures, e.g., above the 85 degrees C for the case of PE. The different set of jaws leaves untouched the compartments and passageways that are to be left with only the blocking attachment. Burst seals 46, 56 are formed either before or after the permanent sealing, using special heating implements heated to a temperature between the blocking temperature and the permanent seal temperature. Finally, liquid reagents are injected through passageways 36, 38, 39, which are then sealed off.

Figure 7:
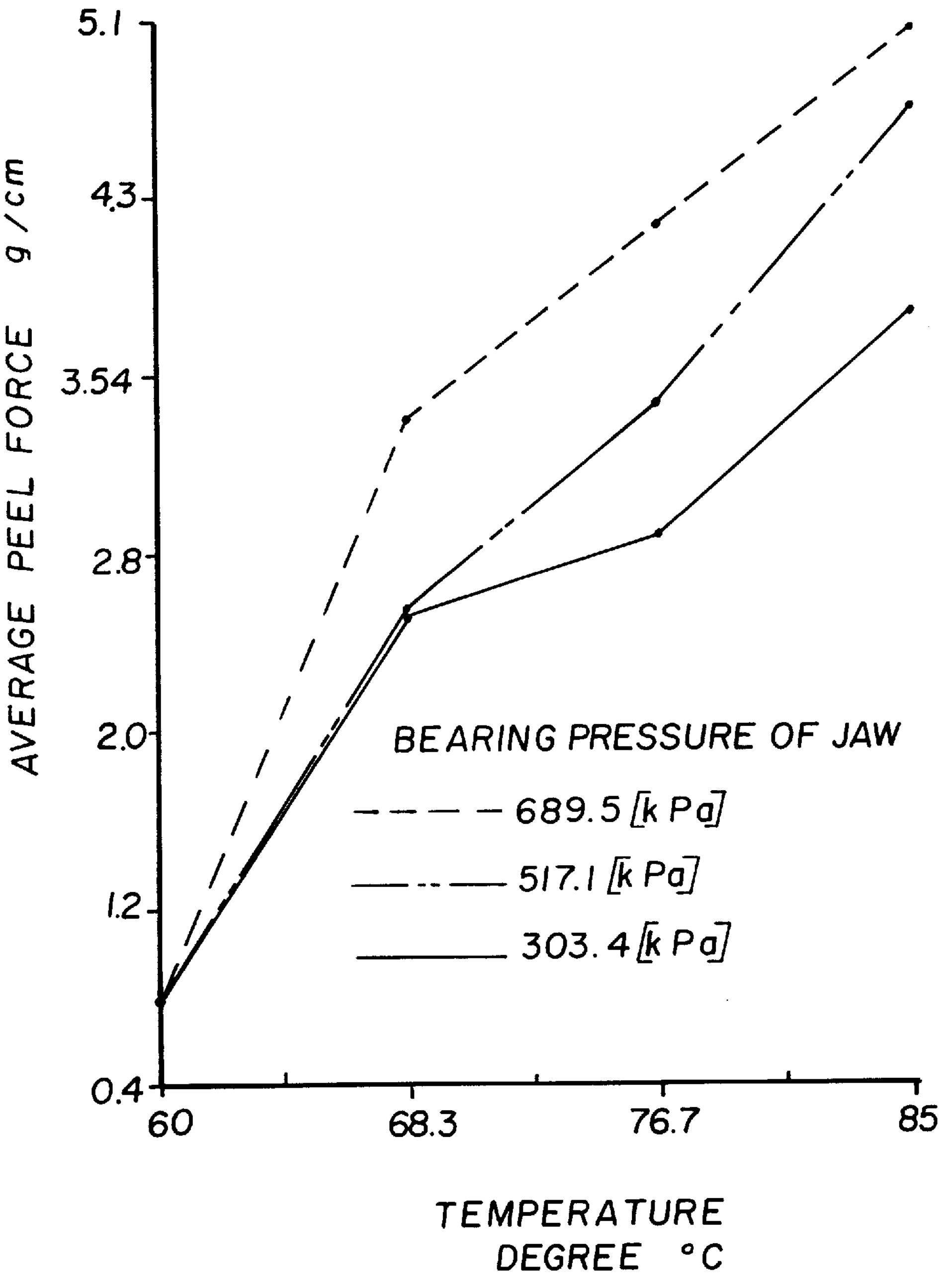

It may be desirable to blend other polymers with the PE, which polymers can affect the peel-apart force that is achieved at a given blocking temperature. For example, in some instances, in order to control the sealing that occurs at temperatures above 85° C., and thus the burst seals that have to be formed, the PE is co-blended with an inhibitor polymer such as polybutylene. It is to be emphasized that this inhibitor polymer is not present to control the blocking phenomenon. However, if it is present, a slightly different plot of peel force versus blocking temperature results, FIG. 7, for substantially the same configuration as shown in FIG. 5, except that some of the inhibitor polymer is blended in with the PE. That is, at a blocking temperature of about 60° C., the peel-apart force is only about 0.8 g/cm instead of the value of about 2.8 g/cm shown in FIG. 6.

An additional option is to apply differing amounts of blocking to different compartments and/or passageways—that is, different blocking temperatures or pressures are applied to different portions, thus creating a different peel-apart force for each different portion.

The invention disclosed herein may be practiced in the absence of any element which is not specifically disclosed herein.

The invention has been described in detail with particular reference to preferred embodiments thereof, but it will be understood that variations and modifications can be effected within the spirit and scope of the invention.

What is claimed is:

1. In a flexible reaction cuvette comprising opposed plastic sheets sealed together to define expandable compartments comprising a sample reaction chamber, a detection chamber, a waste collection chamber, a first passageway between said reaction chamber and said detection chamber, and a second passageway between said detection chamber and said collection chamber;

the improvement wherein said sheets are blocked together in the regions of at least said reaction chamber, said collection chamber, and said passageways by an amount sufficient to require at least 0.8 g/cm of width lineal peel-apart force when peeled at a 90 degree angle, to separate said sheets at said chambers or passageways, but insufficient to permanently adhere the sheets together by an amount that prevents liquid from entering said chambers or passageways;

so that air bubbles are eliminated from the chambers and the passageways prior to initiating flow of liquid into them.

2. A cuvette as defined in claim 1, and further wherein said sheets are blocked together at the region of said detection chamber by said amount.

3. A cuvette as defined in claim 1 or 2, wherein said peel-apart force required to separate said sheets is no greater than about 6 g/cm of width.

4. A cuvette as defined in claim 1 wherein at least one of said sheets comprises polyethylene.

5. A method of forming a sealed compartment between two flexible, plastic sheets so as to eliminate air within the compartment without permanently adhering the sheets together to prevent liquid from entering the compartment, the method comprising:

a) selecting two sheets of plastic having together a heat seal temperature effective to produce a permanent adherence;

b) pressing said sheets together uniformly with a pressure of at least about 300 kPa;

c) heating said sheets in a region of a compartment to a temperature that is sufficient to block the sheets together in said compartment with an attraction requiring a peel-apart force of between about 0.8 and about 6 g/cm of lineal width when peeled at a 90° angle, and is less than said heat seal temperature effective to produce said permanent adherence; and d) heat-sealing the sheets together at at least the heat seal temperature, around at least a portion of the perimeter of the compartment to create a permanent adherence at the perimeter portion.

6. A method as defined in claim 5, wherein at least one of said sheets pressed together comprises polyethylene, and said temperature of heating in step c) is between about 40° C. and about 85° C.

7. A method as defined in claim 5, wherein said uniformly pressing of step b) comprises pressing said sheets between pressure jaws coated with a compliant coating having a durometer value of about 30 durometer Shore “A”.

* * * * *